(12) United States Patent
Zhang

(10) Patent No.: US 10,034,814 B2
(45) Date of Patent: Jul. 31, 2018

(54) MOBILE AUTOMATIC MASSAGE APPARATUS

(71) Applicant: Yizhong Zhang, Singapore (SG)

(72) Inventor: Yizhong Zhang, Singapore (SG)

( * ) Notice: Subject to any disclaimer, the term of this patent is extended or adjusted under 35 U.S.C. 154(b) by 0 days.

(21) Appl. No.: 15/309,034

(22) PCT Filed: Mar. 30, 2015

(86) PCT No.: PCT/SG2015/050053
§ 371 (c)(1),
(2) Date: Nov. 4, 2016

(87) PCT Pub. No.: WO2015/187092
PCT Pub. Date: Dec. 10, 2015

(65) Prior Publication Data
US 2017/0079871 A1    Mar. 23, 2017

(30) Foreign Application Priority Data

Jun. 2, 2014   (SG) ............................ 10201402803R

(51) Int. Cl.
*A61H 7/00*    (2006.01)
*A61H 23/00*   (2006.01)
(Continued)

(52) U.S. Cl.
CPC ........... *A61H 7/004* (2013.01); *A61H 23/004* (2013.01); *A61H 39/007* (2013.01); *A61H 39/04* (2013.01);
(Continued)

(58) Field of Classification Search
CPC ...... A61H 7/004; A61H 39/04; A61H 39/007; A61H 23/004; A61H 2201/5061; A61H 2205/062; A61H 2205/081
See application file for complete search history.

(56) References Cited

U.S. PATENT DOCUMENTS 6,267,737 B1 *  7/2001  Meilus ................... A61H 1/008
                                                    601/108
7,142,945 B2 *  11/2006  Wang ....................... B25J 5/007
                                                    318/568.11
(Continued)

FOREIGN PATENT DOCUMENTS

| CN | 102715887 A | 10/2012 |
|----|-------------|---------|
| CN | 202757270 U | 2/2013 |
| GB | 1522935 A   | 8/1978  |

OTHER PUBLICATIONS

International Search Report for International Application No. PCT/SG2015/050053 dated Aug. 7, 2015.

*Primary Examiner* — Timothy Stanis
(74) *Attorney, Agent, or Firm* — Carter, Deluca, Farrell & Schmidt, LLP

(57) ABSTRACT

A mobile automatic massage apparatus which includes a base of an automatic guided vehicle and a few robotic arms attached above it. A 3D scanner on the pole behind the touch screen monitor takes images of the surrounding environment and guides the movement of the vehicle and positioning of the arms. The hands attached to the robotic arms perform the massage according to the programs of a central computer. This massage apparatus can perform similar professional massage provided by the physicians or therapists to improve the blood circulation of the patients and reduce the pain.

6 Claims, 4 Drawing Sheets

(51) Int. Cl.
*A61H 39/00* (2006.01)
*A61H 39/04* (2006.01)

(52) U.S. Cl.
CPC .. *A61H 2023/002* (2013.01); *A61H 2201/501* (2013.01); *A61H 2201/5028* (2013.01); *A61H 2201/5061* (2013.01); *A61H 2205/04* (2013.01); *A61H 2205/062* (2013.01); *A61H 2205/081* (2013.01); *A61H 2209/00* (2013.01)

(56) References Cited

U.S. PATENT DOCUMENTS

| | | | | |
|---|---|---|---|---|
| 2001/0014781 | A1* | 8/2001 | Nissim | A61H 7/001 601/133 |
| 2003/0032901 | A1* | 2/2003 | Webb | A61H 37/00 601/49 |
| 2005/0143679 | A1* | 6/2005 | Gelber | A61H 7/005 601/15 |
| 2008/0051682 | A1* | 2/2008 | Thomas | A61H 1/0266 601/23 |
| 2009/0271033 | A1* | 10/2009 | Van Der Tol | A01J 5/0175 700/245 |
| 2010/0191160 | A1* | 7/2010 | Avramovich | A61H 7/004 601/94 |
| 2012/0310119 | A1* | 12/2012 | Salo Darder | A61H 37/00 601/6 |
| 2014/0215684 | A1* | 8/2014 | Hardy | A41D 19/0031 2/160 |

* cited by examiner

MOBILE AUTOMATIC MASSAGE APPARATUS

CROSS REFERENCE TO RELATED APPLICATIONS

This application is a national stage application of International Application No. PCT/SG2015/050053, filed Mar. 30, 2015, which claims the benefit of and priority to Singapore Patent Application No. 10201402803R, filed Jun. 2, 2014, the entire contents of each of which are hereby incorporated by reference herein in their entireties.

FIELD OF THE INVENTION

This invention relates to massaging apparatus and more particularly a practical automatic massage apparatus which can free the massage therapists from repeated and tiring physical works. Due to the widely usage of computer and smart phones, nowadays many people experience neck pain, stiff shoulder or lower back pain. Some people may even have cervical spondylitis or sciatica at a very young age. As many people prefer more natural and conservative treatments to control the pain, massage is usually used as a safe alternative. However, due to the shortage of manpower in Singapore and worldwide, the lack of massage therapists become a real problem, especially with the increasing demand from the rapid aging population. And unfortunately, in this tight labour market, a lot of massage therapists lack even the most basic training in orthopedics and rehabilitation. Therefore, the development of a practical, reliable and low-cost robotic professional massaging apparatus is critical and necessary in providing a better healthcare for the public in future. Moreover, this invention can be used as a valuable research tool in evaluation of the effectiveness of traditional Chinese medical massage and other types of massage by providing pre-programed massage with controlled force and techniques.

DESCRIPTION OF THE PRIOR ART

The past massaging apparatus are mostly designed based on the concepts of mechanical movement of certain embodiments of the chairs and beds. They are either massage chair or massage beds. The massage chairs are mostly sold as home applicant and not designed or used for clinical purpose. They cannot provide the massage up to the standard of human therapists.

The massaging beds are mostly invented in China. These past inventions are huge or unable to move freely. However, in real clinics, the equipment is better to be smaller and able to move freely with the physicians or be able to adjust itself to fit to the posture of the patients. The past inventions do not have 3D scanning system so that their massage devices are unable to achieve similar precise movements or adjust the device according to the postures or positions of the patients compared to the current invention.

This invention combines the mobility of automatic guided vehicle and the freely moved reliable robotic arms to provide systematic and accurate massage treatments with more flexibility. It can provide continuous services to patients with the pre-programmed massage techniques under the supervision of the physicians. Moreover, the treatment data recorded by the apparatus also have tremendous research value because it can provide information for researchers in the evaluation of the effectiveness of different massage treatments under the standards of evidence-based medicine.

SUMMARY OF THE INVENTION

In view of the foregoing disadvantages inherent in the known types of massaging devices now present in the prior art, the present invention provides a new and improved way of developing massage apparatus.

This automatic massage apparatus consists of a freely moved automatic guided vehicle as a base which carries one or more robotic arms above it. The touch screen monitor on the top of the vehicle provides information to the user and receives commands from the user as well. The apparatus has a 3D scanner on the top of a supporting pole which can rotate freely depending on the needs. The 3D scanner takes images of the human body and surrounding environment, and transfers the data of the 3-dimensional coordinates of the body and corresponding surrounding objects to the central processing computer which connects the vehicle through Wi-Fi connection. Then the computer directs the vehicle to approach the body and move the artificial hands with the robotic arms to the surface of the body to apply the massage.

The tips of the fingers of the artificial hands have sensors below the soft pads which measure the pressure which are exerted on the body and send the data back to the central computer simultaneously to ensure the effectiveness as well as the safety of the automatic massage process.

The hands are covered by soft materials and warmed by thermal heaters to human temperature to ensure the touching sensation to be soft and comfortable.

The robotic arm moves in certain pattern to enable the fingers and hands to perform the pressing, rubbing, other man-like massage manipulating techniques.

Between the hand and the arm, there is a safety unit which contains a pressure sensor. It will stop the supply of power immediately if the force provided by the arm exceeds this safety level.

Moreover, there is a small remote control unit given to the patient to perform simple adjustments, such as stopping the massage or reducing the strength of massage for safety purpose. If the patient feels that the massage is too painful, they can press the remote control to reduce the strength or even stop the massage.

The power is provided by the batteries placed at the bottom of the apparatus or from a direct power point. There is a separated charging bay connected to the power point. The automatic massage apparatus will automatically return to the charging bay to charge itself to the full amount when it is not working.

In summary, when a patient need to have a massage for certain problem or certain part of the body, the central computer will bring in the medical record of the person and choose a suitable pre-designed massage program under the supervision of the physician. The 3D scanner will take images of the body and the surrounding environment to guide the vehicle to approach the body and apply the suitable massage by the hands attached to the robotic arms. The strength is carefully controlled with the feedback from the pressure sensors. When the massage is completed, the apparatus will return to the charging bay and charge itself.

BRIEF DESCRIPTION OF THE DRAWINGS

The invention will be more readily understood with reference to the accompanying drawing, wherein:

FIG. 1, FIG. 2a, FIG. 2b, FIG. 3a, FIG. 3b and FIG. 4 are not drawn to scale and it shall be noted that the entire assembly may be of different shapes and sizes suitable for the various target areas of application on the body.

Figure 1:
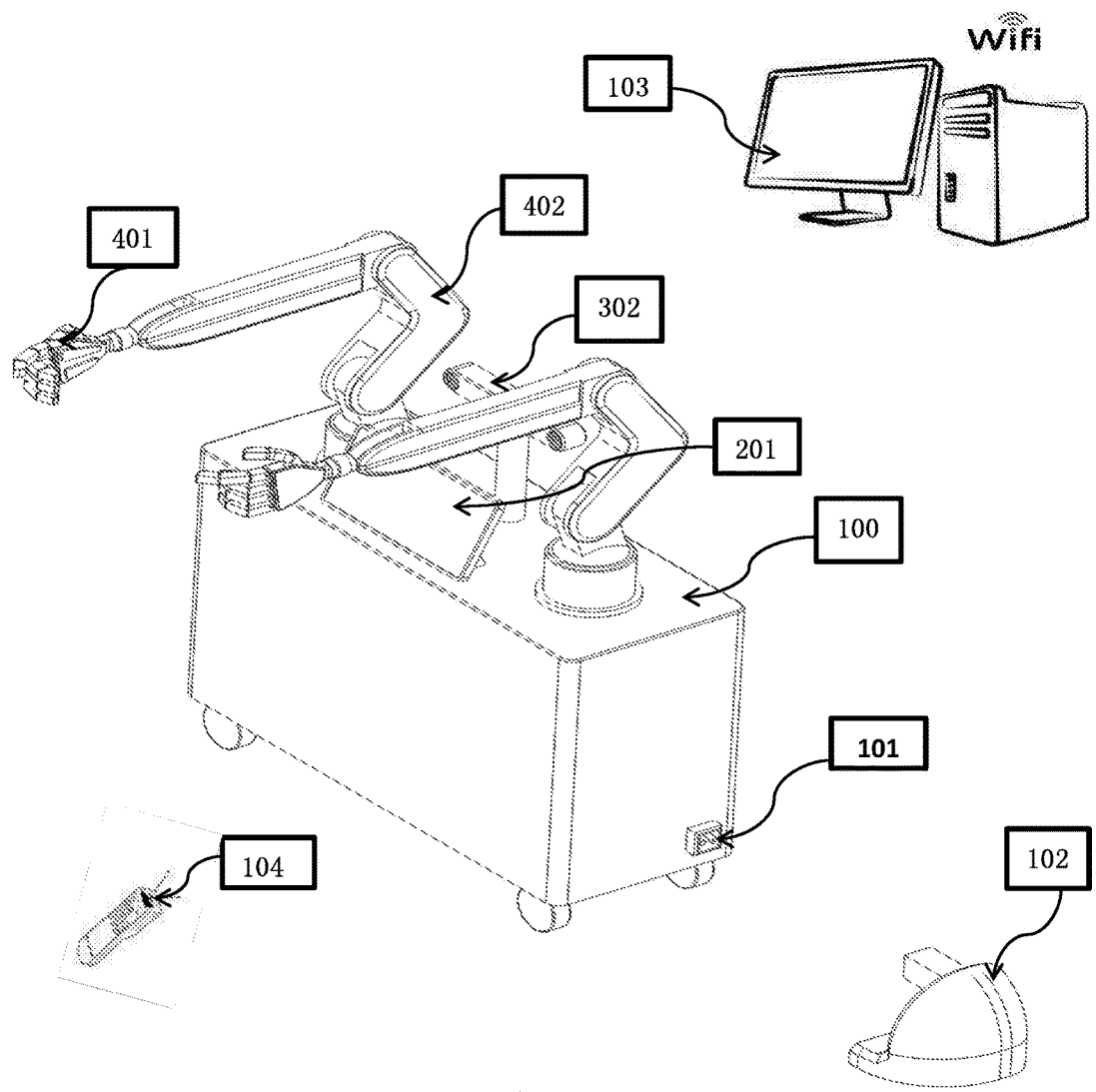
FIG. 1 is an external perspective view of the whole automatic massage system which the invention disclosed in this specification may be applied.

Alternative embodiments of the invention will be apparent to those skilled in the art from consideration of the specification and practice of the invention disclosed herein. It is intended that the specification and examples be considered as exemplary only, with a true scope and spirit of the invention being indicated by the claims.

DETAILED DESCRIPTION OF THE INVENTION

The detailed description describes the invention as it may be used to provide therapeutic or relaxation massage to patients. It is to be understood that these are merely examples of the types of massages in which the invention may be used. Traditional massage requires a high level of physical work and years of medical training which is necessary to enable the therapists to grasp related anatomy knowledge and practical massage techniques. With the robotically assisted system, the massage can be conducted according to the will of the physician or therapist at ease. The automatic massage apparatus allow the physician to choose the most suitable massage procedures for the patients with precisely controlled strength.

The embodiments of the present invention are now discussed, referring to the drawings.

FIG. 1 shows a perspective view of the automatic massage system constructed in accordance with the present disclosure. An automatic guided vehicle 100 is shown to be the mobile base of the massage apparatus which can move freely and tracklessly within a work space guided by the central computer 103 according to the requirement of the physician and the location of the patient. It has battery inside which can provide the power to the vehicle and the other electronic devices of the apparatus, such as robotic arm 402, touch screen monitor 201 and 3D scanner 302. There is a charging bay 102 connected to the normal power point on the wall. The apparatus can return to the charging bay to charge itself by moving itself to the charging bay and attaching the charging unit 101 to the charging bay when the apparatus does not have subsequent work plan.

One or more robotic arms 402 can be attached to the vehicle to facilitate the massage. In FIG. 1, two robotic arms are attached to the vehicle to form the massage apparatus for demonstration purpose. More robotic arms could be attached to conduct more complicated procedures. The robotic arm demonstrated here is a commonly used industrial 6-axis robotic arm. It is important to be noted that it is not confined to certain kinds of robotic arms to develop the automatic massage apparatus for this invention. Different kinds of robotic arms with different number of axis could be used to fulfill the spirit of this invention. Each robotic arm 402 may be supported by the vehicle and move according to the massage program selected by the physician from the remote central computer 103.

The touch screen monitor 201 could show the life status of the patient such as temperature, blood pressure and heart rate during massage. It could be used as an input/output device to control the program as well.

A remote control 104 given to the patient allows the patients to do simple adjustments including change of the level of massage strength and shut down the power of the whole apparatus.

When certain massage program started, the 3D scanner 302 on the pole 301 behind the touch screen monitor 201 will take the images of the human body and the surrounding objects to locate the human body and record the coordinates of all related objects. These data are sent to the central computer and processed to direct the apparatus to approach the human body and lower the robotic arm 402 to the human body to apply the massage.

Figure 2A:
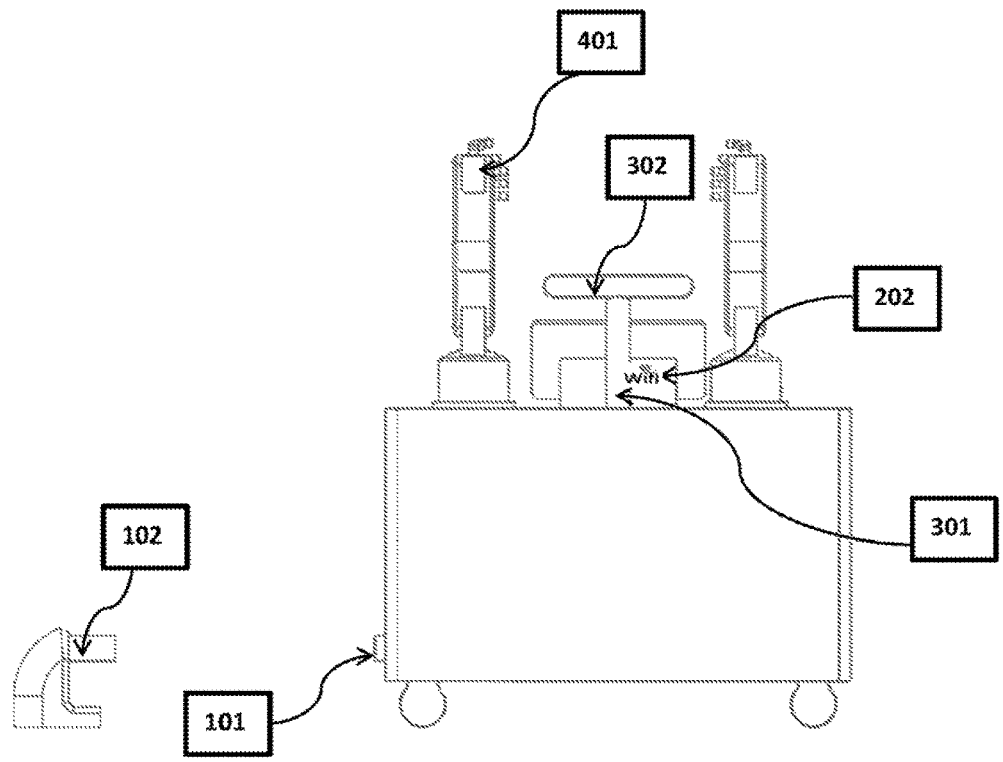
FIG. 2a is the back view of the automatic massage apparatus.
Figure 2B:
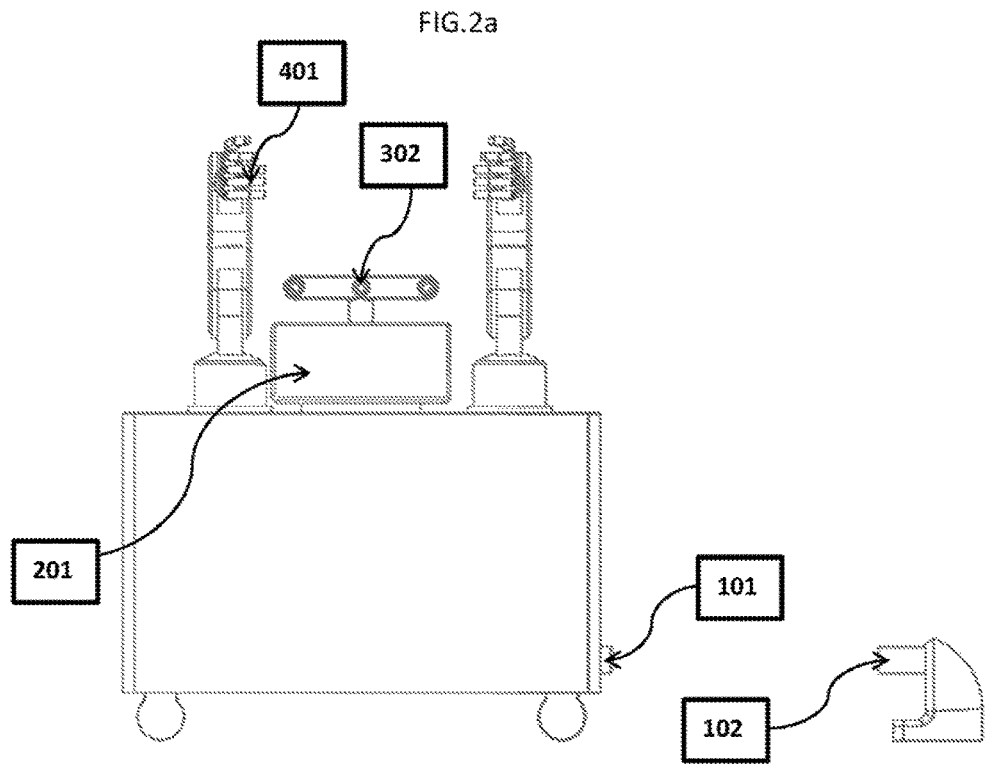
FIG. 2b is the front view of the automatic massage apparatus.

The central computer 103 connects to the apparatus through Wi-Fi connection unit 202 shown in FIG. 2a. There is a robotic hand 401 with flexible fingers attached to each robotic arm.

Figure 3A:
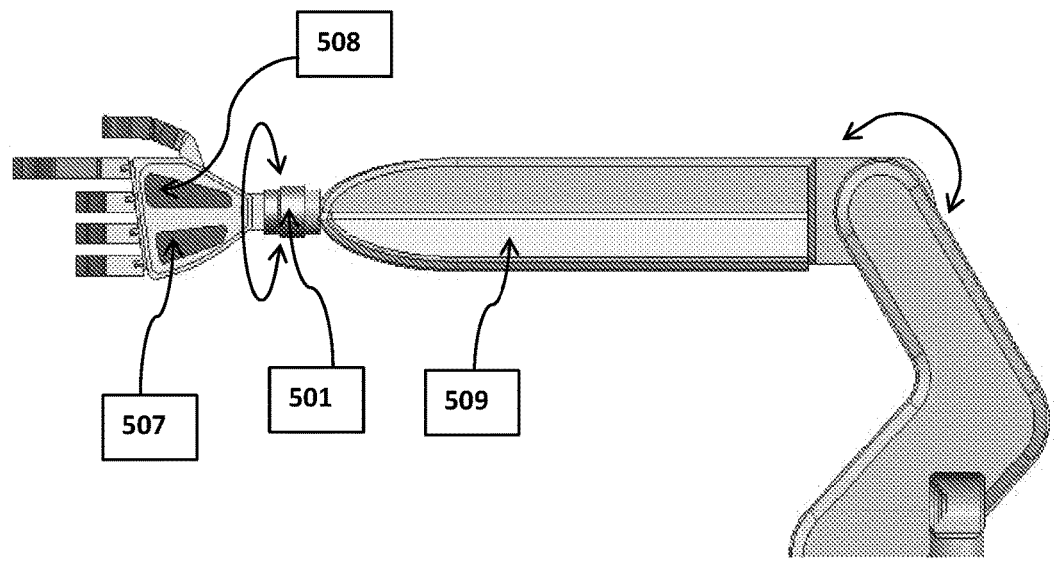
FIG. 3a is an enlarged view of the front part of the robotic arm of the automatic massage apparatus.

FIG. 3a shows an enlarged view of a portion of FIG. 1 to give a better view of the robotic arm. The robotic arm 402 may include one or more servo motors to move the arm to a desired position. There is a long soft pad 509 attached below the forearm of the robotic arm. The massage could be applied by the portion 509 below the forearm of the robotic arm or the hands 401 attached to the arm. The soft pad could be made of soft materials such as rubber or other soft material with the pressure sensors and thermal heater beneath it.

As FIG. 3a has demonstrated, there is a safety unit 501 between the hand and the arm. This safety unit can rotate freely while measuring the force passed to the hand by the robotic arm. It will cut the power supply of the massage apparatus when the force exceeds certain safety level and other precaution measures fail to work. This is to ensure the ultimate safety for patients.

Figure 3B:
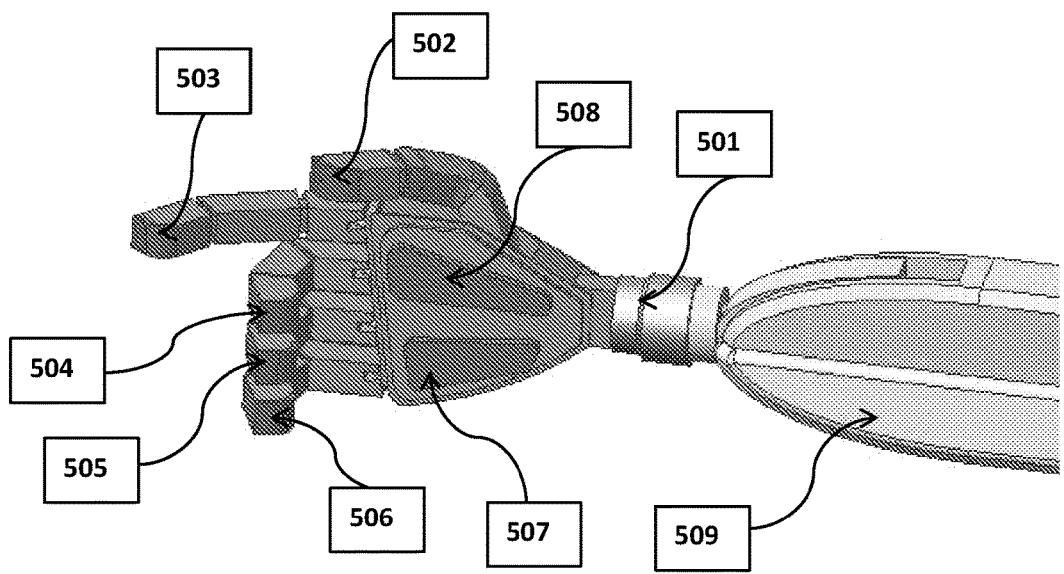
FIG. 3b is an enlarged view of the hand attached to the robotic arm.

FIG. 3b shows an enlarged view of a portion of FIG. 1 to give a better view of the hand 401 attached to the robotic arm. The fingers and the palm have soft pads as well. These soft pads have similar structure as the soft pad attached to the forearm. The fingers of the hands have soft pads 502 503 504 505 506 attached to them. The palm has softs pads 507 508 attached. The thermal heaters inside the soft pads increase the temperature of the robotic hands to approximately 38 degree Celsius and sustain the temperature at the suitable level.

Figure 4:
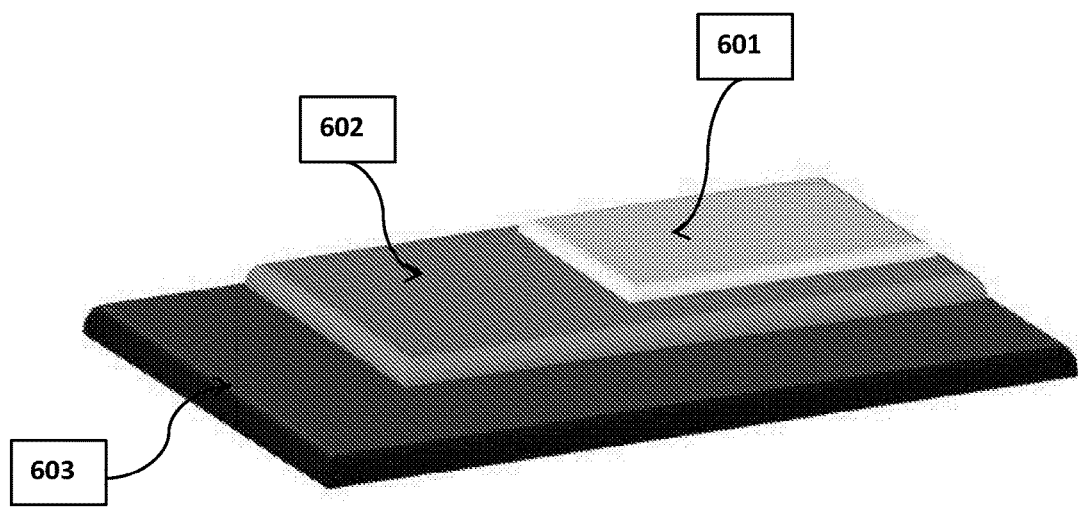
FIG. 4 is cross-sectional view showing the three layer structure of the soft pads attached to the robotic arms and hands.

FIG. 4 shows a cross section view of the soft pad which represents three layers of the soft pad. The outer layer 601 is made of soft materials. The central layer 602 contains pressure sensors which monitor the pressure constantly. The inner layer 603 contains thermal heater which can increase the temperature of the pad and the robotic arm from room temperature to approximately 38 degree Celsius.

The invention claimed is:

1. A mobile automatic massage apparatus for improving peripheral vascular blood circulation and reducing soreness or pain of a human body, the mobile automatic massage apparatus comprising:

an automatic guided vehicle as a mobile base configured to move without assistance of tracks to approach the human body;

a three-dimensional (3D) scanner configured to obtain 3D data of the human body and surrounding objects, to guide the mobile automatic massage apparatus, and to monitor treatment;

a touch screen monitor configured to provide an input and output interface;

a remote central computer configured to operate massage programs and send instructions to the mobile automatic massage apparatus through a wireless connection;

one or more robotic arms configured to move freely in any direction;

a forearm operatively attached to a distal end of each robotic arm and configured to directly massage targeted positions;

a hand operatively attached to the forearm and configured to directly massage the targeted positions;

soft pads with a three layer structure including a soft material layer, a pressure sensor layer and a thermal heater layer;

artificial hands covered by the soft pads which are configured to perform different techniques of massage;

a communication unit configured to transfer the 3D data between the mobile automatic massage apparatus and the remote central computer;

a remote control configured to allow a patient to perform simple adjustments including stopping the massage or reducing a strength of the massage for safety purposes;

a power stopper configured to stop a supply of power immediately when force exerted on the human body exceeds a safety level; and a charging bay configured to allow the mobile automatic massage apparatus to return to the charging bay to charge itself when it is not performing a massage.

2. The mobile automatic massage apparatus according to claim 1, wherein the power stopper includes a pressure sensor configured to measure force passed to the hand by the one or more robotic arms.

3. The mobile automatic massage apparatus according to claim 1, wherein the power stopper is positioned between the hand and the forearm.

4. The mobile automatic massage apparatus according to claim 3, wherein the power stopper includes a pressure sensor configured to measure force passed to the hand by the corresponding robotic arm.

5. The mobile automatic massage apparatus according to claim 1, wherein a lower portion of the forearm is configured to directly massage the targeted positions.

6. The mobile automatic massage apparatus according to claim 5, wherein the lower portion of the forearm is covered by a soft pad.

* * * * *